(12) United States Patent
Thramann et al.

(10) Patent No.: US 7,621,928 B2
(45) Date of Patent: *Nov. 24, 2009

(54) ANEURYSM STENT

(75) Inventors: Jeffery Thramann, 8580 Strawberry La., Longmont, CO (US) 80503; Michael Fulton, Superior, CO (US)

(73) Assignee: Jeffery Thramann, Longmont, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/756,238

(22) Filed: May 31, 2007

(65) Prior Publication Data

US 2007/0225794 A1    Sep. 27, 2007

Related U.S. Application Data

(63) Continuation of application No. 10/680,063, filed on Oct. 6, 2003, now Pat. No. 7,241,301.

(51) Int. Cl.
*A61B 17/08* (2006.01)

(52) U.S. Cl. .................................... 606/157

(58) Field of Classification Search ............... 606/108, 606/151, 157, 158, 191, 195, 198, 200; 623/1.11, 623/1.12, 1.2
See application file for complete search history.

(56) References Cited

U.S. PATENT DOCUMENTS

| | | | |
|---|---|---|---|
| 5,405,379 A | | 4/1995 | Lane |
| 5,527,338 A | | 6/1996 | Purdy |
| 5,693,067 A | * | 12/1997 | Purdy ......................... 606/200 |
| 5,935,148 A | * | 8/1999 | Villar et al. ................. 606/213 |
| 5,980,554 A | | 11/1999 | Lenker et al. |
| 6,010,517 A | | 1/2000 | Baccaro |
| 6,036,720 A | | 3/2000 | Abrams et al. |
| 6,086,577 A | | 7/2000 | Ken et al. |
| 6,168,615 B1 | | 1/2001 | Ken et al. |
| 6,168,622 B1 | | 1/2001 | Mazzocchi |
| 6,309,367 B1 | | 10/2001 | Boock |
| 6,346,117 B1 | | 2/2002 | Greenhalgh |
| 6,350,270 B1 | | 2/2002 | Roue |
| 6,375,668 B1 | | 4/2002 | Gifford et al. |
| 6,383,174 B1 | | 5/2002 | Eder |
| 6,432,128 B1 | | 8/2002 | Wallace et al. |
| 6,454,780 B1 | | 9/2002 | Wallace |
| 6,463,317 B1 | | 10/2002 | Kucharczyk et al. |
| 6,551,303 B1 | * | 4/2003 | Van Tassel et al. .......... 604/104 |
| 6,605,111 B2 | * | 8/2003 | Bose et al. ................. 623/1.18 |
| 6,790,218 B2 | | 9/2004 | Jayaraman |
| 2001/0000797 A1 | | 5/2001 | Mazzocchi |
| 2002/0120297 A1 | | 8/2002 | Shadduck |
| 2002/0143349 A1 | | 10/2002 | Gifford, III et al. |

OTHER PUBLICATIONS

International Bureau: Notification of Transmittal of The International Search Report and the Written Opinion of the International Searching Authority, or the Declaration Oct. 11, 2005.

* cited by examiner

*Primary Examiner*—Kevin T Truong
(74) *Attorney, Agent, or Firm*—Holland & Hart LLP

(57) ABSTRACT

The present invention relates to an aneurysm stent having a base and connector. The base has a vessel facing side and an aneurysm facing side, and is shaped to cover an aneurysm sufficiently. The connector is coupled to the aneurysm facing side of the base such that when deployed the connector is adapted to extend partially into the aneurysm to anchor the base about the aneurysm and alter flow into the aneurysm. Further, the stent can be used as a delivery mechanism to deliver growth factor.

20 Claims, 9 Drawing Sheets

ANEURYSM STENT

The present application is a continuation of U.S. patent application Ser. No. 10/680,063, filed Oct. 6, 2003, titled Aneurysm Stent with Growth Factor, allowed, which is a continuation-in-part of U.S. patent application Ser. No. 10/455,145, filed Jun. 4, 2003, titled Aneurysm Stent, which claims the benefit of U.S. Provisional Patent Application Ser. No. 60/404,422, filed Aug. 19, 2002, titled A Cerebral Aneurysm Coil Sent, both of which are incorporated herein by reference.

FIELD OF THE INVENTION

The present invention relates to the surgical repair of aneurysms and, more particularly, to a patch that provides a seal between the arterial wall and a neck of the aneurysm to alter flow in the aneurysm.

BACKGROUND OF THE INVENTION

An aneurysm is a blood-filled dilation of a blood vessel. Major concerns with aneurysms revolve around rupturing of the arterial wall causing internal bleeding and clots breaking away from the aneurysm causing strokes.

There exist two generally approved methods of treating aneurysms. The first method of treatment includes surgical treatment. The second method of treatment includes endovascular treatment. Surgical removal of the aneurysm is sometimes not possible, leaving endovascular treatment as the only available option. Even when not the only option, endovascular treatment often is preferred because of the reduced risks and complications.

Conventionally, endovascular treatment of an aneurysm involves "packing" the aneurysm such that an endovascular occlusion is formed. Packing the aneurysm with coils, such as Guglielmi Detachable Coils (or GDCs), helps form an occlusion. While using GDCs is conventional, the aneurysm can be packed with numerous devices, such as, for example, other types of coils, balloons, glues, polymers, clotting agents, liners, or the like. Recent studies have found, however, that the body breaks down conventional treatments re-exposing blood flow to the aneurysm.

Endovascular treatment, while considered less risky than surgical treatment, has other drawbacks as well. One drawback of endovascular treatment of the aneurysm includes the potential to over pack the aneurysm. Over packing the aneurysm can cause the material to enter the parent blood vessel, potentially altering blood flow in the remaining vessel or generating undesirable pressure in the aneurysm. Also, some aneurysms have a wide connection to the blood vessel, a.k.a. wide neck aneurysms. Wide neck aneurysms have the additional risk that the occluded material will break free of the aneurysm and enter the parent blood vessel, potentially causing blockage of the parent blood vessel. Finally, clotting agents and polymers used to form occlusions in the aneurysm can seep to the parent blood vessel causing complications. Balloons and liners are intuitively pleasing as a solution, but have the potential for an inexact fit causing complications. For example, a balloon may be over inflated causing unwanted pressure or under inflated causing seepage in the aneurysm.

While the packing methods described above alter blood flow to the aneurysm, the aneurysm neck typically is open to the parent blood vessel. Thus, blood continues to flow to the aneurysm. To reduce the blood flow, several devices have been developed to cover the neck area of the aneurysm.

U.S. Pat. No. 6,454,780, issued Sep. 24, 2002, to Wallace, titled Aneurysm Neck Obstruction Device, shows a device designed to cover or block the neck of the aneurysm. FIG. 1 shows the Wallace device 10 in some detail. The device 10 is placed inside aneurysm 50 using a catheter 46 and deployment tool 44. When inside the aneurysm 50, device 10 has walls 12 that expand or unfold to contact the inside of the aneurysm 50 and block neck 51. But the device resides internal to aneurysm 50 allowing blood flow shown by arrow A in the parent vessel 52 to push up against the walls 12. The upward pressure of the blood vessel on the wall 12 may allow blood from the parent vessel to seep in aneurysm 50. Also, because the wall is internal to the aneurysm 50, the neck 12 has the potential to expand. Other types of internal devices include liners and other neck bridges.

Devices to block the neck of the aneurysm external to the aneurysm exist also. These devices use the pressure of the blood vessel to help seat the block against the parent vessel wall and shield the neck from the blood vessel. One such device is shown in U.S. Pat. No. 6,309,367, issued Oct. 30, 2001, to Boock, titled Aneurysm Shield. The Boock device is shown in FIG. 2. The Boock device 30 has a cylindrical shaft 32 that covers the neck 37 of the aneurysm 38 and is anchored by anchor rings 34 and 36. While device 30 resides external to the aneurysm it has multiple parts that could break free or deteriorate that reside in the parent vessel. While the Boock device 30 seemingly works for its intended purpose in theory, its relatively large size and surface area makes its impractical to actually use. In the brain, for example, multiple blood vessels may branch off from the location of an aneurysm. Attempting to use the Boock device would block blood flow to one or more of the branch vessels as well as the aneurysm, which makes the Boock device useful in only limited situations, if any.

Thus, it would be desirous to develop and improve internal and external aneurysm stents. Further, it would be desirous to develop a device capable of delivering growth factor to the aneurysm neck to promote aneurysm neck occlusion.

SUMMARY OF THE INVENTION

To attain the advantages and in accordance with the purpose of the invention, as embodied and broadly described herein, apparatuses to alter the flow of blood to an aneurysm comprise a base and connector. The base has a vessel facing side and an aneurysm facing side, and is shaped to cover an aneurysm sufficiently. The connector is coupled to the aneurysm facing side of the base such that when deployed the connector is adapted to extend partially into the aneurysm that has been pre-packed with Guglielmi Detachable Coils and couple to the coils to anchor the base about the aneurysm and alter flow into the aneurysm.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
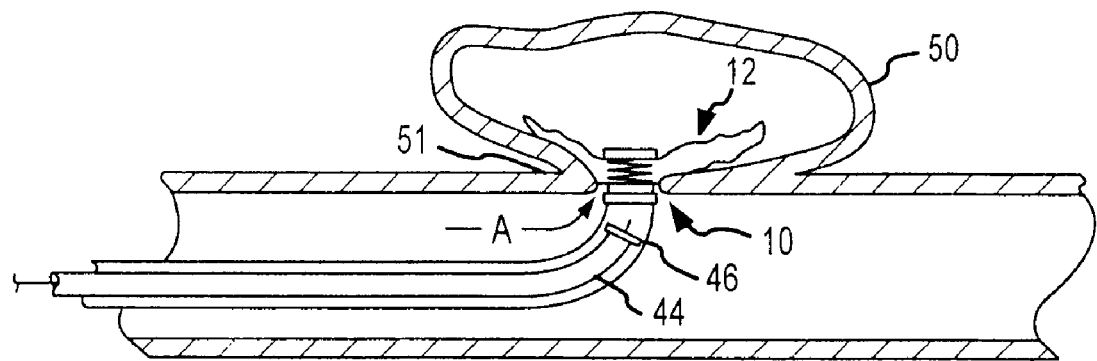
FIG. 1 shows a prior art aneurysm device.
Figure 2:
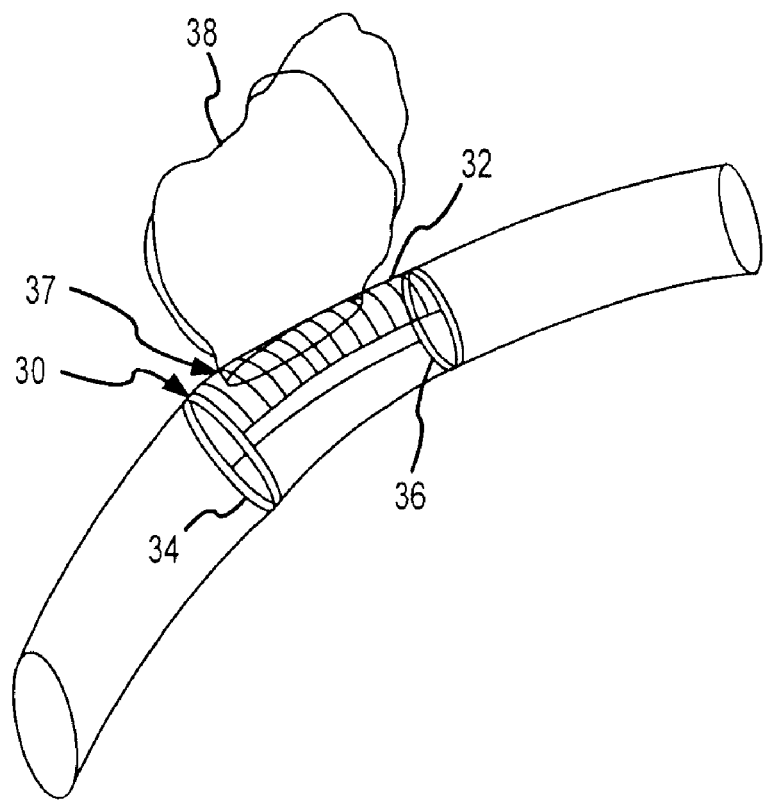
FIG. 2 shows a prior art aneurysm device.
Figure 3:
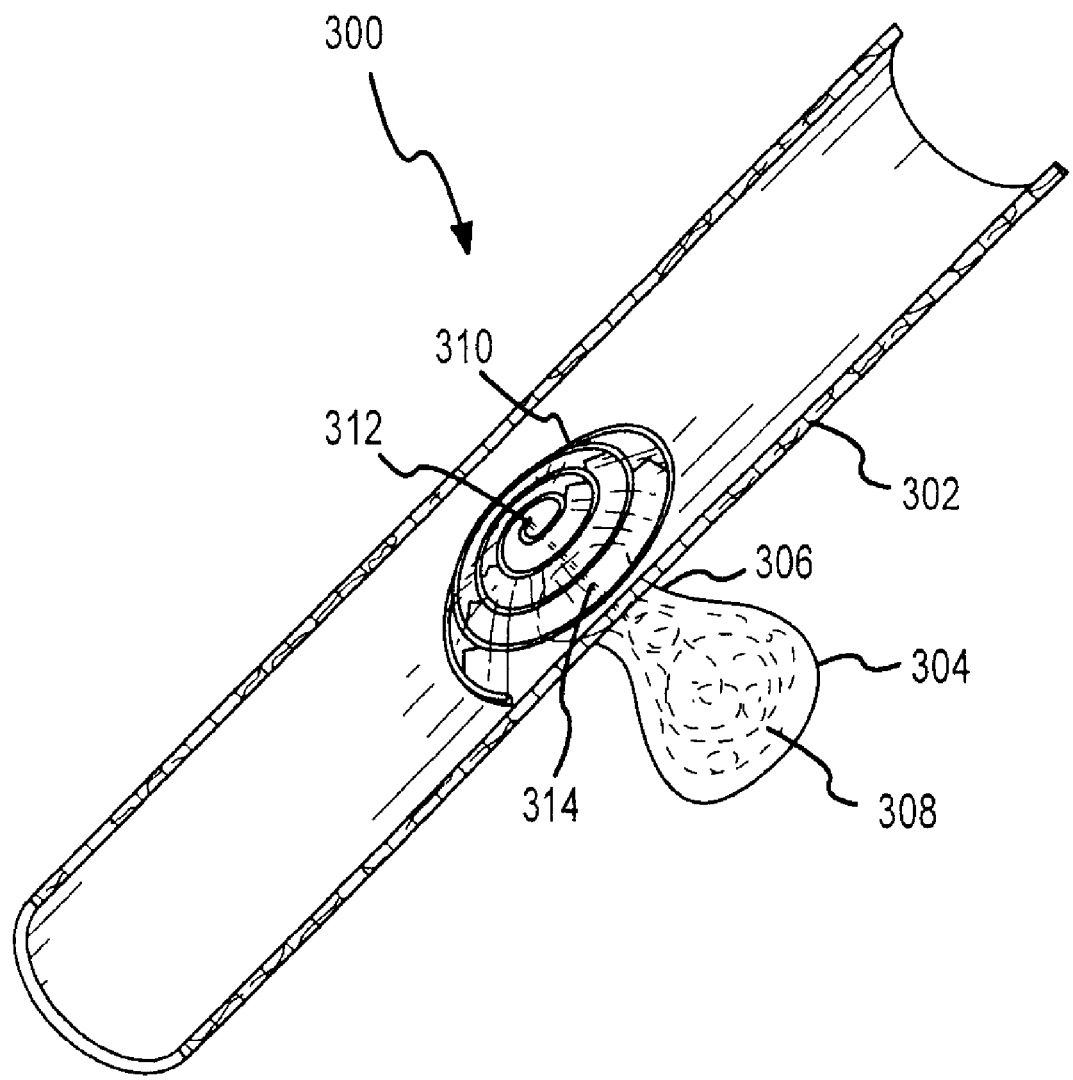
FIG. 3 shows a perspective view of an aneurysm stent deployed in a blood vessel illustrative of the present invention.

Some embodiments of the present invention are described with reference to FIGS. 3 to 10B. FIG. 3 shows an aneurysm stent 300 consistent with an embodiment of the present invention deployed. Stent 300 is deployed in a parent blood vessel 302, which is shown as an artery but could be a vein a capillary, or the like, about aneurysm 304. A blood flow path from vessel 302 to aneurysm 304 is provided by an aneurysm neck 306. Neck 306 is shown as a narrow neck, but could be a wide neck. Aneurysm 304 is shown packed with conventional GDCs 308. While shown as packed with conventional coils, aneurysm 304 could be packed with any type of packing agent, such as, for example, other types of coils, balloons, glues, polymers, clotting agents, liners, or the like. In fact, aneurysm 304 does not need to be packed at all as stent 300 blocks blood flow to aneurysm 304. The attachment of stent 300 to cover neck 306 will depend, in part, on the type of material used to pack aneurysm 304, if any. While FIG. 3 (and FIGS. 6 and 7 below) shows the stent of the present invention completely occluding the neck of the aneurysm, one of ordinary skill in the art on reading the disclosure will recognize that completely occluding the neck is desirable but unnecessary. In other words, the present invention need only be sufficiently aligned to substantially occlude the neck to function.

Instead of using, for example, GDCs to pack the aneurysm, the aneurysm 304 could be packed with special growth coils that are designed to deliver growth factors to the aneurysm 304 in order to stimulate thrombus organization or enhance fibrosis formation and endothelialization within the aneurysm 304 and across the neck. By promoting this type of growth within the aneurysm, the possibility of preventing aneurysm recurrence is minimized. These growth coils are positioned in the aneurysm 304 in the same manner as a conventional GDC 308. The growth coils comprise a carrier, a binder, and a growth factor. The carrier material forms the backbone or helical structure of the coil but is selected to ensure a controlled release of the growth factor. The carrier material includes but is not limited to polyethylene terephthalate (PET) and polyvinyl alcohol (PVA). The binder material helps bind the growth factor to the carrier in a manner that does not interfere with the release of the growth factor into the aneurysm 304. The binder material includes but is not limited to gelatin hydrogel. The growth factor is a material that is designed to directly stimulate thrombus organization in the aneurysm 304 by allowing cells to promote their migration and proliferation. The growth factor includes but is not limited to basic fibroblast growth factor (bFGF), transferring growth factor, and vascular endothelial growth factor. It is believed the growth factor would be most efficient if it was delivered about the neck of the aneurysm. Thus, these same materials can be used on stent 300 in order to promote fibrosis growth, as will be explained below.

With reference to FIG. 3, which illustrates aneurysm 304 packed with conventional GDCs 308, stent 300 includes a base 310, a base connection point 312, and a connector 314. Base 310 has opposed sides, a vessel side and a wall side (not specifically labeled). The vessel side can be covered with a graft material or other biocompatible material. The vessel side and or the wall side may be coated with a material to stimulate cell growth and encourage formation of a pseudo-intima. Moreover, base 310, as mentioned above, is substantially aligned with neck 306 of aneurysm 304. Being aligned with the neck makes base 310 a good carrier, but not the only possible carrier, for the growth factor identified above. Placing the growth factor on either the vessel facing side or wall facing side of base 310 would encourage growth such that the new growth would, hopefully, occlude neck 306. In this case, base 310 would comprise the carrier, binder, and growth factors described above. In addition, the wall side could be covered with an adhesive to assist in seating stent 300 about neck 306 by forming a seal between base 310 and vessel 302. Base connection point 312 couples base 310 to connector 314. Base connection point 312 does not need to exist as a separate component, but is identified for convenience to distinguish between base 310 and connector 314. Base connection point 312 could, as a matter of design choice, be a fitting to connect base 310 and connector 314 if desired. Connector 314 can be a conventional coil material attached to base 312 that extends to GDCs 308. When deployed, connector 314 assumes its coiled shape and engages GDCs 308 to assist in keeping stent 300 seated about neck 306. Connector 314 could physically curl around or hook into GDCs 308 for anchoring, but connector 314 could simply pack in aneurysm 304 similar to a conventional GDC. Connector 314 could simply anchor stent 300 in place, but could also contract and pull base 310 snug against vessel 302 to firmly seat base 310 about aneurysm neck 306 further altering blood flow to aneurysm 304. While only one base connection point 312 and one connector 314 is shown in FIG. 3, multiple connections and connectors are possible. Also, the connections do not necessarily have to be in the center of the stent, but could be offset. It is believed greater stability will be obtained by symmetrical placement of connectors and connection points, but asymmetrical placement is possible. Multiple connectors could be attached to a single connection point as well.

Figure 4:
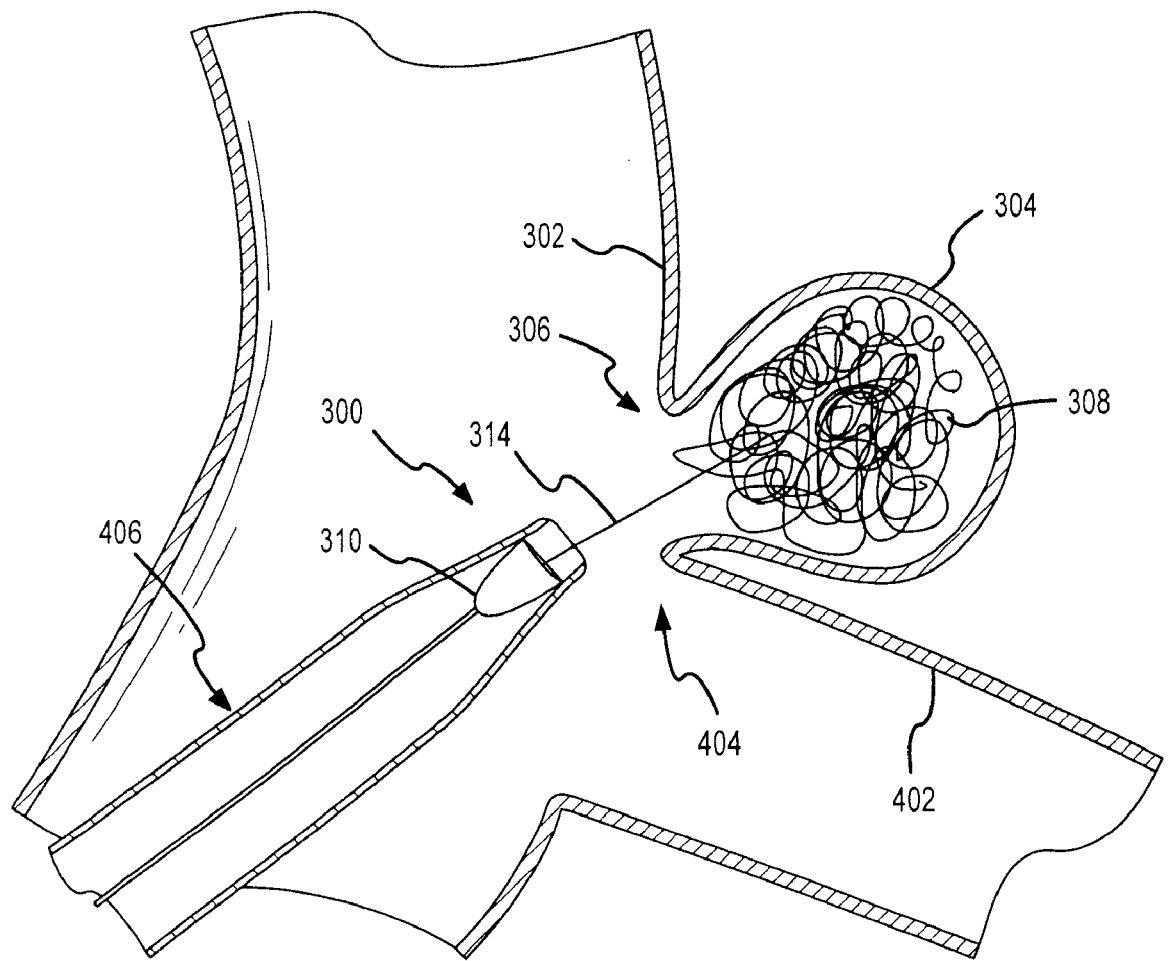
FIG. 4 shows a cross section of a blood vessel with an aneurysm prior to deployment of the aneurysm stent illustrated in FIG. 3.
Figure 5:
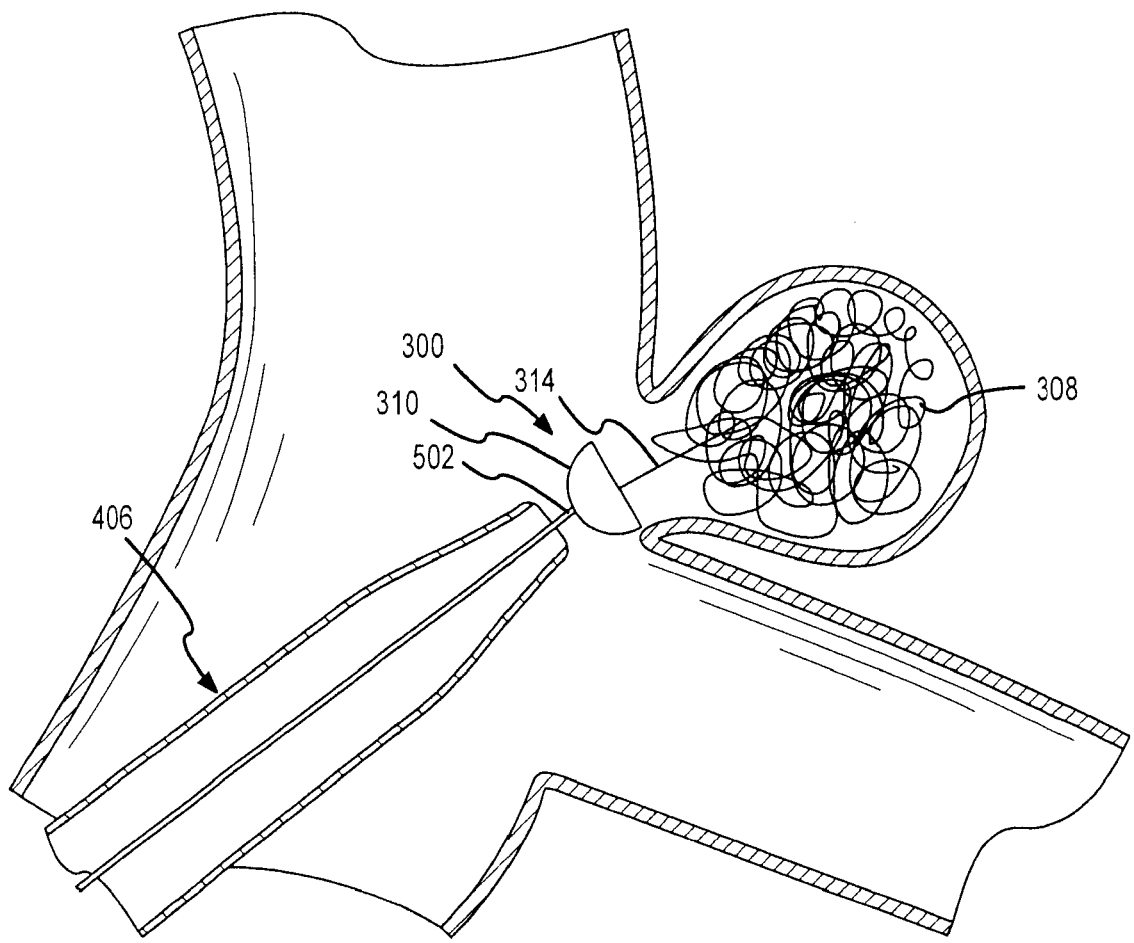
FIG. 5 shows a cross section of the aneurysm stent just prior to deployment.

Referring now to FIGS. 4-7, a method of deploying the stent 300 will be described. Referring first to FIG. 4, parent vessel 302 is shown with aneurysm 304 and neck 306 existing off the main body of vessel 302. Unlike FIG. 3, a second vessel 402 resides about neck 306 forming a junction 404. While the present invention will be explained in connection with deploying stent 300 about junction 404, stent 300 could be similarly deployed at locations with more or less junctions. First, aneurysm 304 is packed using, for example, conventional GDCs 308 or special growth coils in a conventional manner. Without going in much detail, GDCs 308 are placed by first directing a catheter 406 to the site of aneurysm 304. GDCs 308 are passed through catheter 406 and packed in aneurysm 304 in a conventional manner. Once GDCs 308 are placed, stent 300 is passed through the same or a different catheter 406 using a guide wire 502 (FIG. 5). Stent 300 includes base 310 and connector 314. As can be seen, base 310 is compacted to pass through catheter 406. Also, connector 314 enters the packed GDCs 308.

Referring now to FIG. 5, stent 300 has exited catheter 406 and guide wire 502 can be seen attached to stent 300. Base 310 is approaching neck 306 and connector 314 has extended in GDCs 308 packed in aneurysm 304. As shown, base 310 can be made of a self-expanding material that begins expanding on exiting catheter 406. Alternatively, base 310 can be made of a material that requires activation or other manipulation to expand.

Figure 6:
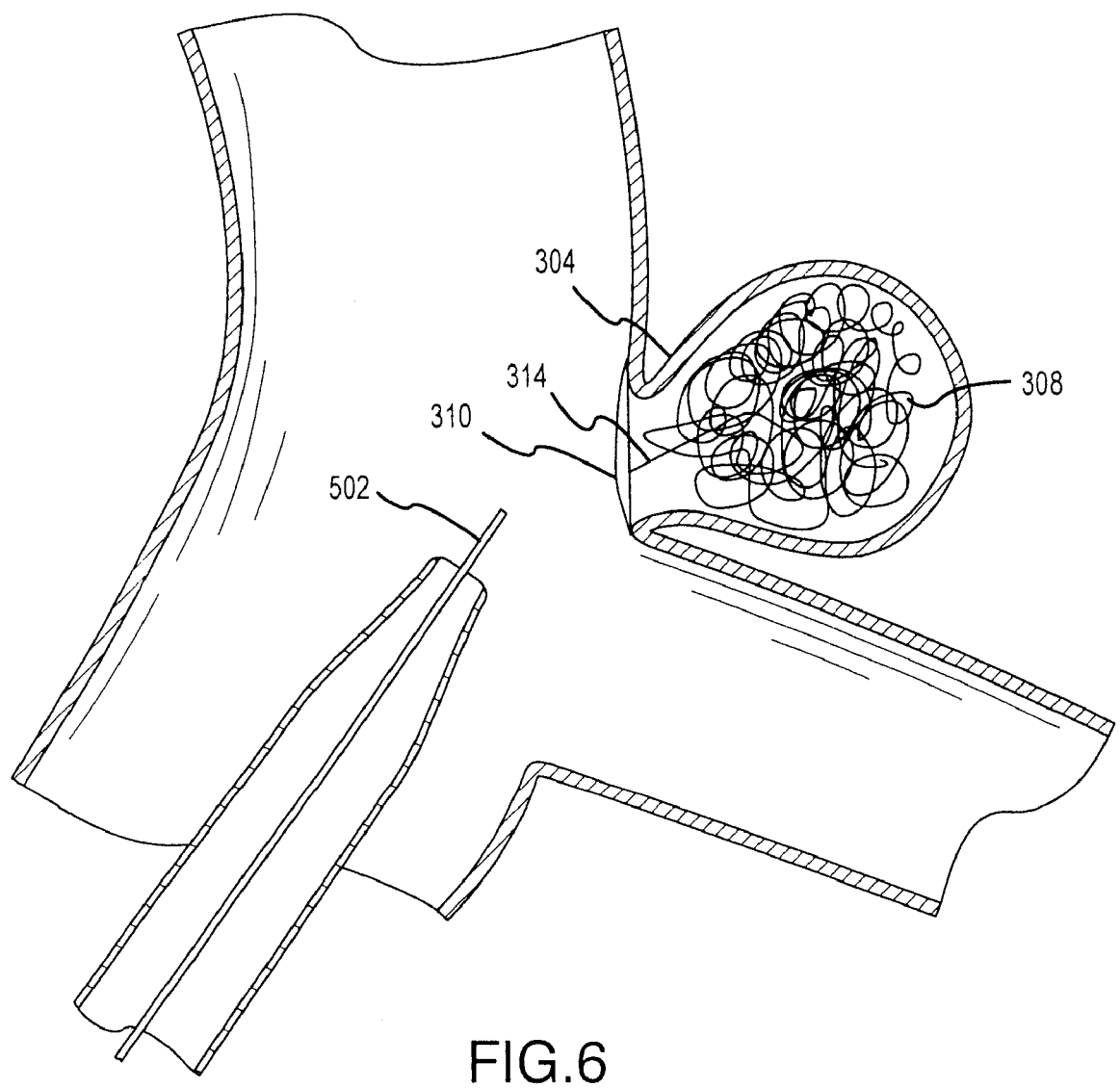
FIG. 6 shows a cross section of the aneurysm stent mostly deployed about the aneurysm.

Referring now to FIG. 6, stent 300 is shown in the appropriate position and guide wire 502 has been withdrawn. Base 310 has expanded sufficiently to mostly block neck 306 and connector 314 has begun curling, packing, embedding or otherwise anchoring in aneurysm. For example, connector 314 can be placed about GDCs 308 as conventional packing material, connector 314 can curl and engage GDCs 308, or the like. While one connector 314 is shown, it would be possible to have two of more connectors 314. As described in more detail below, a number of other devices and techniques can be used to anchor stent 300 about the neck.

Figure 7:
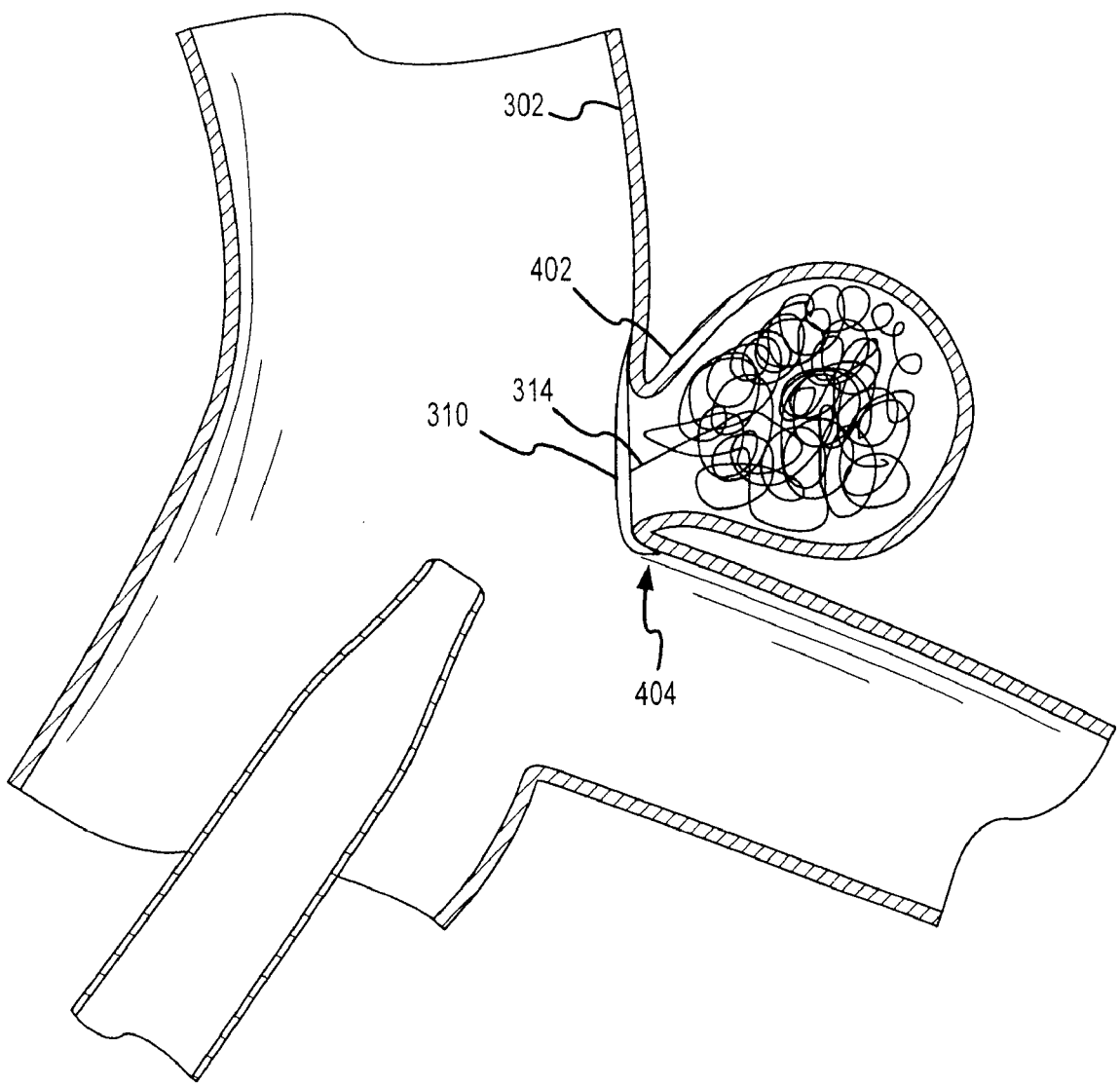
FIG. 7 shows a cross section of the aneurysm stent deployed.

Referring now to FIG. 7, stent 300 is shown with base 310 and connector coils 314 fully deployed. In this case, base 310 is flush with the wall of vessel 302, wraps around junction 404 and is flush with the wall of vessel 402. Connectors 314 are engaged with GDCs 308 and, optionally, connectors 314 contract in a manner that pulls base 310 in toward GDCs 308 providing a snug seating between base 310 and vessel 302. Ideally, base 310 completely occludes aneurysm 304; however, it is more typical for base 310 to substantially occlude aneurysm 304.

The stent 300 could be made of many materials. Some material includes conventional graft material. Alternatively, stent 300 could be made of one or more shaped memory alloys (SMAs) or a combination of graft material and SMAs. SMAs are a group of materials that demonstrate an ability to return to some previously defined shape or size when subjected to the appropriate thermal procedure. Generally, these materials can be plastically deformed and, upon exposure to thermal manipulation, will return to the pre-deformation shape. Some SMA material is considered to be two-way shaped memory alloys because they will return to the deformed shape upon proper thermal activation. SMAs include Ag—Cd alloys, Cu—Al—Ni alloys, Cu—Sn alloys, Cu—Zn alloys, Cu—Zn—Si alloys, Cu—Zn—Sn alloys, Cu—Zn—Al alloys, In—Ti alloys, Ni—Al alloys, Ni—Ti alloys, Fe—Pt alloys, Mn—Cu alloys, Fe—Mn—Si alloys, and the like. As shown by FIGS. 4-7, SMAs would work well for stent 300 because, for example, connectors 314 could be shaped with a predefined curl that will engage GDCs 308. The SMA could be deformed at a predefined temperature to a straight, or substantially straight, shape to allow for connectors 314 to penetrate packed GDCs 308 in aneurysm 302. Thermal manipulation would cause connector coils 314 to assume the original curled shape that will anchor stent 300 about aneurysm 302 and may provide a force tending to pull base 310 in towards aneurysm 302 further seating stent 300 about aneurysm 302. Similarly, base 310 could be made of SMA. In this case, base 310 could be originally shaped to approximate the shape of the vessel(s) around aneurysm neck 304 to allow for as close a fit as possible. This would also allow use of stent 300 in areas having many vessels branching around the aneurysm.

Figure 8:
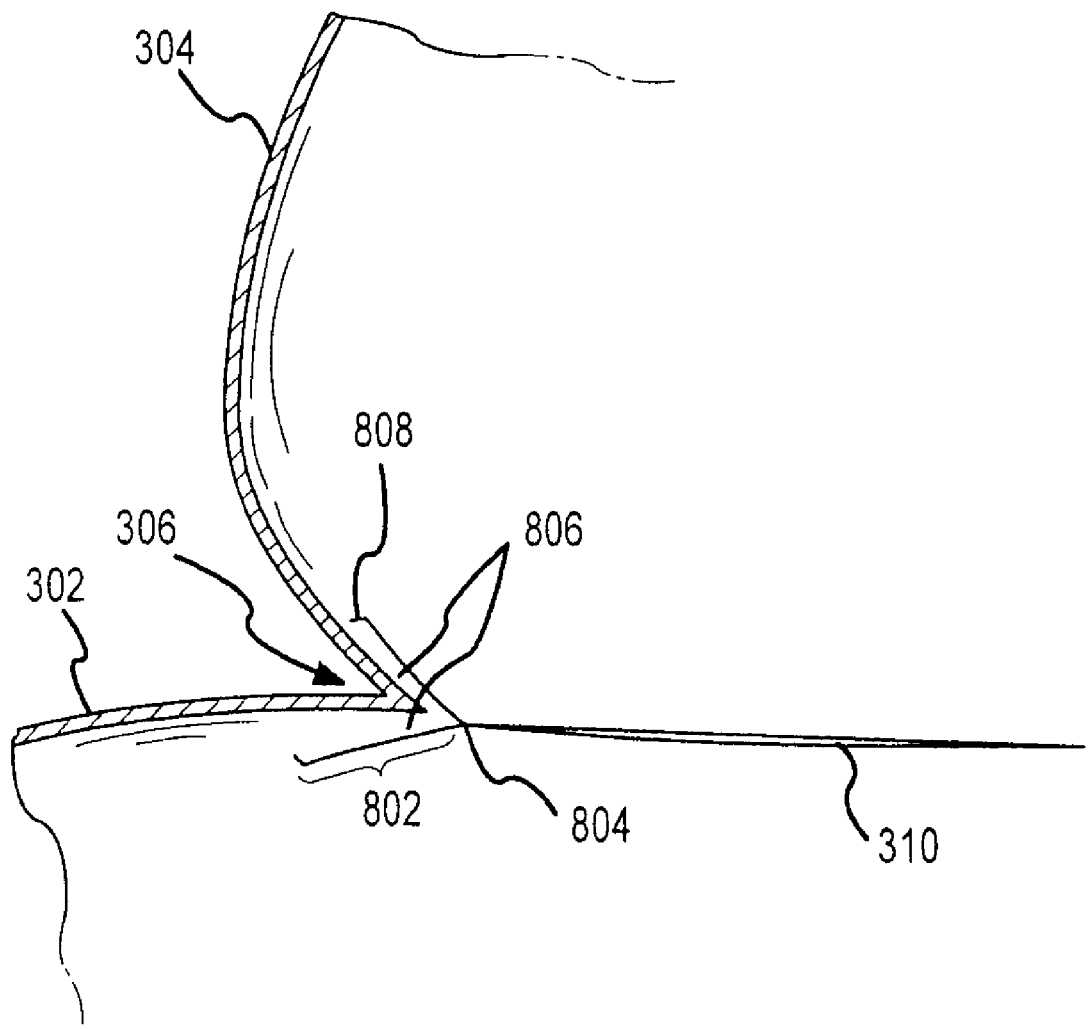
FIG. 8 shows a cross section of a portion of a stent consistent with the present invention.

As shown in FIGS. 3-7, base 310 is shown having a circular or semi-circular shape. In particular, FIG. 3 illustrates base 310 as a coil of material that expands on deployment. The shape of base 310, however, is largely a function of material, design choice, and the aneurysm location. Thus, stent 300 could take many shapes including triangular, rectangular, square, elliptical, conical, spherical, circular, cylindrical, or the like The present invention has been described with the aneurysm packed with conventional GDC coils, as described above, the aneurysm could be packed with alternative material. For example, if the aneurysm was packed with a polymer or clotting agent, the connector or anchor could be a simple post connected to the stent and embedded in the occlusion. Base 310 connected to the post would be held in place by the occlusion. Further seating force could be supplied by using a material that contracts on activation, such as SMAs. If the aneurysm was packed with a liner or balloon, a connection post could be provided on the balloon or liner to allow attaching the stent to the balloon or liner. For example, a balloon inserted in aneurysm 302 could have a flanged lower post (similar to some helium balloons) that connector coil 314 could wrap around. In this case, if, for example, connector coil 314 was made out of SMAs, thermal activation could cause coil 314 to tighten around the post attached to the balloon and contract. The contraction would be resisted by the flange on the post tending to pull base 310 in towards aneurysm 302 to assist in seating base 310 about aneurysm 302. Alternatively to a post, the stent could have prongs that extend along the inside walls of the aneurysm such that the expanded balloon or liner would press the prongs against the wall of the aneurysm and seat the stent. Referring to FIG. 8, base 310 could be designed with a clamp 802 around an edge 804 of base 310. As shown, clamp 802 could have opposed surfaces 806 such that when deployed, surfaces 806 move together and grip vessel 302 at neck 306. A ridge 808 could be provided to assist in the grip. Clamp 802 would be particularly useful if aneurysm 304 was not packed with anything.

Figure 9A:
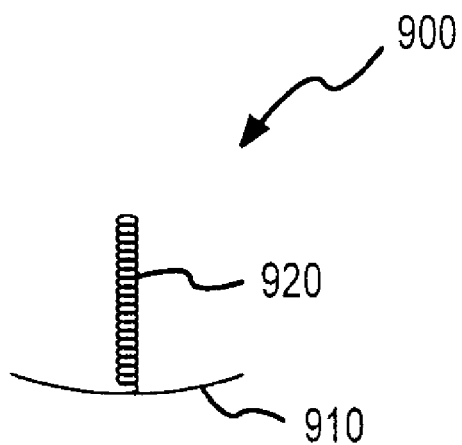
FIGS. 9A and 9B show a stent consistent with the present invention.
Figure 9B:
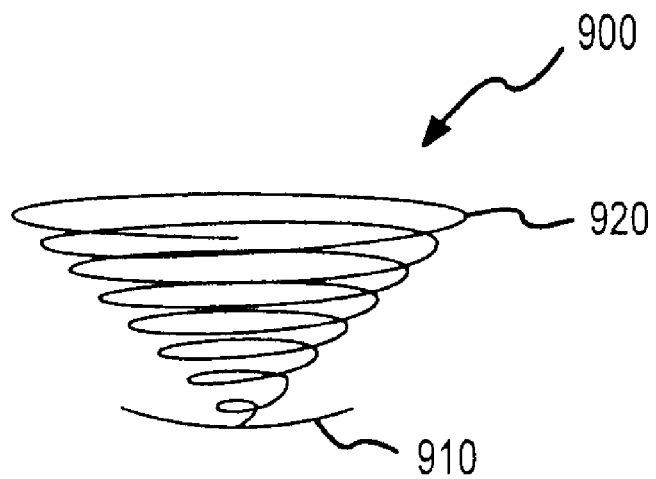

Referring to FIGS. 9A and 9B, another stent 900 consistent with the present invention is shown. Stent 900 includes a base 910 and a connector 920. Undeployed, connector 920 is a tightly wrapped coil of material. On deployment, connector 920 unwinds into a bulbous or volumous area sufficiently to anchor the stent 900. Generally, connector 920 would expand to completely fill aneurysm space, but at a minimum the expansion should be sufficient to prevent connector 920 from pulling out of the aneurysm. As can be appreciated, stent 900 could be used to treat the aneurysm without packing material. But if packing material were used to treat the aneurysm, connector 920 would not need to expand as much. In addition, the connector 920 could be composed of a material to promote fibrosis growth in the aneurysm as described above.

Figure 10A:
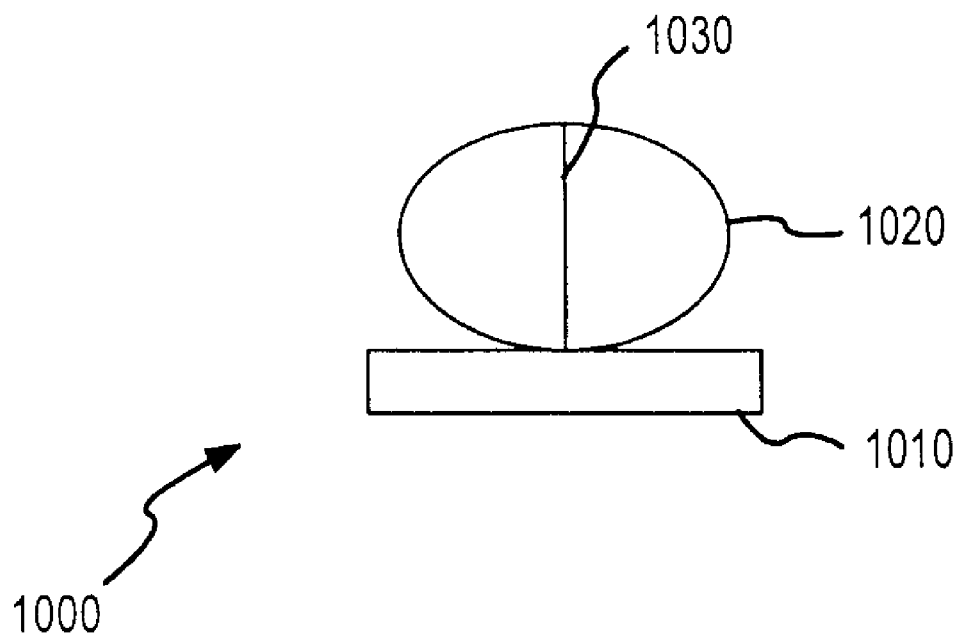
FIGS. 10A and 10B show a cross-section of a stent consistent with the present invention.
Figure 10B:
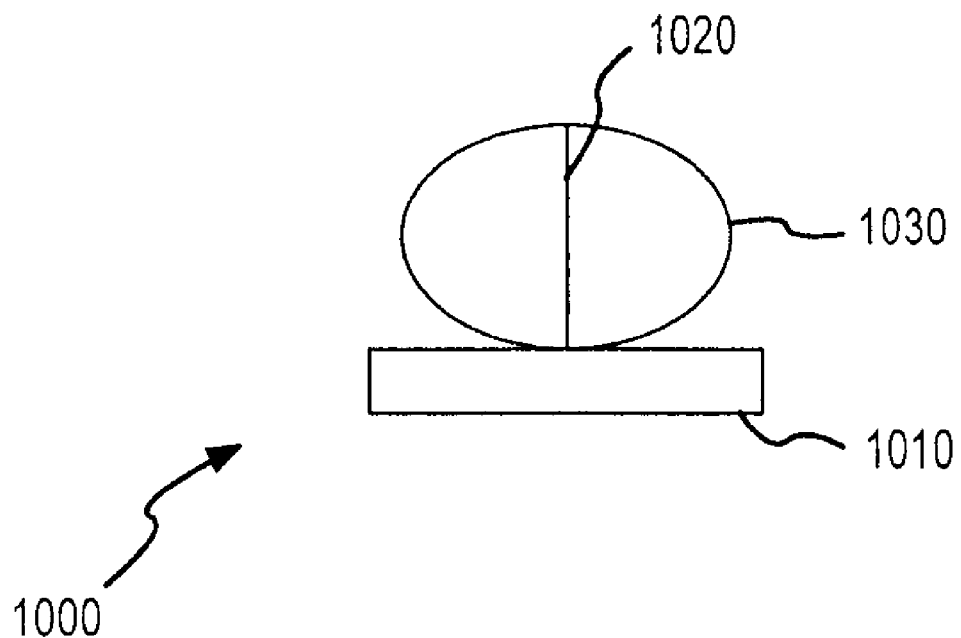

FIGS. 10A and 10B show another stent 1000 consistent with the present invention. FIG. 10A shows a front plan view of a stent 1000 that includes a base 1010 and expanded connectors 1020 and 1030. While stent 1000 is shown with two orthogonal rings as connectors 1020 and 1030, more rings could be used. Further the rings could be cross-linked or individual rings. FIG. 10B shows a side plan view of stent 1000 also with expanded connectors 1020 and 1030. As can be seen, connectors 1020 and 1030, which are shown in the deployed state, expand to form rings that act similar to the corkscrew anchor above. Also, while shown as rings any shape is possible, such as diamond, circular, square, triangular, elliptical, helical, or the like.

While the invention has been particularly shown and described with reference to a preferred embodiment thereof, it will be understood by those skilled in the art that various other changes in the form and details may be made without departing from the spirit and scope of the invention.

We claim:

1. An apparatus to inhibit flow to an aneurysm packed with coils, the apparatus comprising:
 a base having a vessel facing side and an aneurysm facing side;
 the base when deploy being larger than a neck of the aneurysm and comprising a shape sufficient to cover the neck of the aneurysm such that the base is adapted to remain in the vessel and external to the aneurysm whereby blood flow through the vessel is maintained; and
 a connector attached to the aneurysm facing side of the base, the connector comprising at least a connector coil, at least the connector coil is adapted to extend from the base only partially into the aneurysm, the connector coil couples to the coils packed in the aneurysm when deployed,
 wherein the connector is adapted to anchor the base about the aneurysm to inhibit flow into the aneurysm.

2. The apparatus according to claim 1, wherein the connector and connector coil are specially designed not to pierce a wall of the aneurysm.

3. The apparatus according to claim 1, wherein the coils packed in the aneurysm comprise Guglielmi Detachable Coils.

4. The apparatus according to claim 1, wherein the connector coil is a Guglielmi Detachable Coil.

5. The apparatus according to claim 1, wherein the base comprises graft material.

6. The apparatus according to claim 1, wherein the base comprises self-expanding material such that the base can be delivered in a small package and expands on deployment to cover the aneurysm.

7. The apparatus according to claim 6, wherein the base also comprises graft material.

8. The apparatus according to claim 6, wherein the self-expanding material comprises a shaped memory alloy.

9. The apparatus according to claim 1, wherein the at least one connector coil is made of at least a first shaped memory alloy.

10. The apparatus according to claim 9, wherein the at least one connector coil is deformed such that on thermal treatment the at least one connector coil is adapted to engage coils packed in the aneurysm to provide a force tending to seat the base on a vessel wall about the aneurysm.

11. The apparatus according to claim 1, wherein the base resides completely in the vessel.

12. The apparatus according to claim 1, wherein the aneurysm facing side is coated with an adhesive.

13. The apparatus according to claim 1, wherein the base comprises a growth factor.

14. The apparatus according to claim 1, wherein the vessel facing side is coated with a material to stimulate cell growth.

15. An aneurysm treatment system, comprising:
 a plurality of guglielmi detachable coils adapted to be packed in the aneurysm;
 an aneurysm base, the aneurysm base when deployed being larger than a neck of the aneurysm and comprising a shape sufficient to cover the aneurysm such that the aneurysm base is adapted to remain in the vessel and external to the aneurysm whereby blood flow through the vessel is maintained;
 at least one connector coupled to the base adapted to have a portion that extends only partially in the aneurysm; and
 the portion of the at least one connector that extends only partially in the aneurysm adapted to couple to the plurality of guglielmi detachable coils adapted to be packed in the aneurysm.

16. The aneurysm stent treatment system according to claim 15, wherein the at least one connector is coupled to a geometric center of the base.

17. The aneurysm stent treatment system according to claim 16, wherein the at least one connector is at least two connectors, each connector adapted to extent only partially in the aneurysm.

18. The aneurysm stent treatment system according to claim 15, wherein the base has a vessel side and an aneurysm side, the vessel side comprises a layer of biocompatible material that promotes permanent fixation of the stent.

19. The aneurysm stent treatment system according to claim 18, wherein the biocompatible material is a graft coated with a material to stimulate cell growth.

20. The aneurysm stent treatment system according to claim 19, wherein the material to stimulate cell growth is a growth factor.

* * * * *